United States Patent
Long et al.

(10) Patent No.: US 11,896,428 B2
(45) Date of Patent: Feb. 13, 2024

(54) ADAPTIVE SELECTION OF ULTRASOUND FREQUENCY

(71) Applicant: Duke University, Durham, NC (US)

(72) Inventors: James Long, Durham, NC (US);
Nicholas Bottenus, Durham, NC (US);
Willie J. Long, Durham, NC (US);
Gregg E. Trahey, Durham, NC (US)

(73) Assignee: Duke University, Durham, NC (US)

( * ) Notice: Subject to any disclaimer, the term of this patent is extended or adjusted under 35 U.S.C. 154(b) by 210 days.

(21) Appl. No.: 17/080,467

(22) Filed: Oct. 26, 2020

(65) Prior Publication Data

US 2021/0121156 A1    Apr. 29, 2021

Related U.S. Application Data

(60) Provisional application No. 62/925,491, filed on Oct. 24, 2019.

(51) Int. Cl.
*A61B 8/14*  (2006.01)
*G01S 15/89* (2006.01)
*A61B 8/08*  (2006.01)

(52) U.S. Cl.
CPC .............. *A61B 8/14* (2013.01); *A61B 8/5207* (2013.01); *G01S 15/8954* (2013.01); *G01S 15/8959* (2013.01)

(58) Field of Classification Search
CPC ........... A61B 8/14; A61B 8/5207; A61B 8/54; G01S 15/8954; G01S 15/8959;

(Continued)

(56) References Cited

U.S. PATENT DOCUMENTS 4,709,236 A    11/1987  Taylor
5,526,816 A *  6/1996  Arditi ................. G01S 7/52038
                                                600/458

(Continued)

FOREIGN PATENT DOCUMENTS

JP    2012-118040 A    6/2012
KR   10-2007-0050694 A    5/2007

OTHER PUBLICATIONS

Li et al., "Visualization of Small-Diameter Vessels by Reduction of Incoherent Reverberation With Coherent Flow Power Doppler". IEEE Trans Ultrason Ferroelectr Freq Control. Nov. 2016;63(11):1878-1889 teaches ultrasound with short time Fourier transform (Year: 2016).*

(Continued)

*Primary Examiner* — Sean D Mattson
*Assistant Examiner* — Michael Yiming Fang
(74) *Attorney, Agent, or Firm* — Kaplan Breyer Schwarz, LLP

(57) ABSTRACT

An ultrasound system is disclosed. Embodiments in accordance with the present invention include a transducer configured to acquire pulse-echo data at each transmit frequency bandwidth of interest. In addition, a bandpass filter is configured to receive a signal of the pulse-echo data, wherein the signal is bandpass-filtered over a plurality of frequencies. Further, a processor is configured to calculate a spatial coherence of the bandpass-filtered signal. The spatial coherence of the signal is calculated in a spatial domain or a frequency domain. The spatial coherence is used to predict target conspicuity. The processor selects a preferred frequency based on and, preferably, to realize, the target conspicuity.

15 Claims, 7 Drawing Sheets

(58) Field of Classification Search
CPC ............. G01S 7/52042; G01S 15/8915; G01S 15/8981; G06T 2207/10132
See application file for complete search history.

(56) References Cited

U.S. PATENT DOCUMENTS

| | | | |
|---|---|---|---|
| 6,309,357 | B1 | 10/2001 | Guracar et al. |
| 8,684,934 | B2 | 4/2014 | Kim |
| 11,415,693 | B2 | 8/2022 | Long et al. |
| 11,478,218 | B2 * | 10/2022 | Rothberg ................. A61B 8/08 |
| 2004/0037166 | A1 * | 2/2004 | Handa ................. G10K 11/341 367/103 |
| 2005/0049496 | A1 | 3/2005 | Guracar |
| 2005/0054931 | A1 * | 3/2005 | Clark ................. G01S 15/8981 600/453 |
| 2007/0211756 | A1 * | 9/2007 | Glaser-Seidnitzer ........................ A61B 8/565 370/466 |
| 2012/0041309 | A1 * | 2/2012 | Coussios ................. A61B 8/08 600/437 |
| 2013/0109971 | A1 * | 5/2013 | Dahl ................... G01S 7/52046 600/447 |
| 2014/0276055 | A1 * | 9/2014 | Barthe ................. A61B 8/4466 600/439 |
| 2014/0316274 | A1 | 10/2014 | Koh et al. |
| 2015/0003677 | A1 * | 1/2015 | Cho ....................... G06T 7/0012 382/103 |
| 2015/0223903 | A1 * | 8/2015 | Bell ....................... A61B 34/30 901/41 |
| 2015/0272551 | A1 * | 10/2015 | Jung .................... A61B 8/5207 600/443 |
| 2018/0220995 | A1 * | 8/2018 | Pelissier .............. A61B 8/5207 |
| 2018/0345605 | A1 | 12/2018 | Escowitz |
| 2019/0196013 | A1 * | 6/2019 | Stanziola ............ G01S 15/8977 |
| 2019/0380684 | A1 | 12/2019 | Insana et al. |
| 2020/0114596 | A1 | 4/2020 | Davidson et al. |
| 2021/0085293 | A1 * | 3/2021 | Gong ................. G01S 15/8915 |
| 2022/0036545 | A1 * | 2/2022 | St. Pierre ................ A61B 6/502 |

OTHER PUBLICATIONS

Song et al., "Coded excitation for ultrasound tissue harmonic imaging", Ultrasonics, vol. 50, Issue 6, 2010, pp. 613-619, ISSN 0041-624X. (Year: 2010).*

Dahl J, Jakovljevic M, Pinton GF, Trahey GE. Harmonic spatial coherence imaging: an ultrasonic imaging method based on backscatter coherence. IEEE Trans Ultrason Ferroelectr Freq Control. Apr. 2012;59(4):648-59. doi: 10.1109/TUFFC.2012.2243. PMID: 22547276; PMCID: PMC3342045. (Year: 2012).*

Lediju MA, Trahey GE, Byram BC, Dahl JJ. Short-lag spatial coherence of backscattered echoes: imaging characteristics. IEEE Trans Ultrason Ferroelectr Freq Control. Jul. 2011;58(7):1377-88. doi: 10.1109/TUFFC.2011.1957. PMID: 21768022; PMCID: PMC3172134. (Year: 2011).*

Dahl JJ, Hyun D, Lediju M, Trahey GE. Lesion detectability in diagnostic ultrasound with short-lag spatial coherence imaging. Ultrason Imaging. Apr. 2011;33(2):119-33. doi: 10.1177/016173461103300203. PMID: 21710827; PMCID: PMC3141297. (Year: 2011).*

Tartakovsky, Alexander & Brown, James. (2008). Adaptive spatial-temporal filtering methods for clutter removal and target tracking. Aerospace and Electronic Systems, IEEE Transactions on. 44. 1522-1537. 10.1109/TAES.2008.4667727. (Year: 2008).*

Long J., Long W., N. Bottenus, G. F. Pinton and G. E. Trahey, "Implications of Lag-One Coherence on Real-Time Adaptive Frequency Selection," 2018 IEEE International Ultrasonics Symposium (IUS), Kobe, Japan, 2018, pp. 1-9, doi: 10.1109/ULTSYM.2018.8580063 (hereinafter "Long"). (Year: 2018).*

IEEE International Ultrasonics Symposium Program Book, 2018, IEE Ultrasonics, Ferroelectrics, and Frequency Control Society (Year: 2018).*

A. G. Tartakovsky, et al., "Adaptive Spatial-Temporal Filtering Methods for Clutter Removal and Target Tracking," IEEE Transactions—AES, pp. 1-14, Sep. 2007 (Year: 2007).

Bjaerum et al., "Clutter Filters Adapted to Tissue Motion in Ultrasound Color Flow Imaging," IEEE Transactions on Ultrasonics, Ferroelectrics, and Frequency Control, vol. 49, No. 6, pp. 693-704, Jun. 2002 (Year: 2002).

Notice of Allowance issued in U.S. Appl. No. 17/080,527, dated May 11, 2022, 10 pp.

J. Dahl, et al., "Harmonic Spatial Coherence Imaging: An Ultrasonic Imaging Method Based on Backscatter Coherence", IEEE Transactions on Ultrasonics, Ferroelectrics, and Frequency Control, vol. 59, No. 4, pp. 648-659, Apr. 2012 (Year: 2012).

C. Kasai et al., "Real-Time Two-Dimensional Blood Flow Imaging Using an Autocorrelation Technique," in IEEE Transactions on Sonics and Ultrasonics, Dec. 1, 1985, doi: 10.1109/T-SU.1985.31615, pp. 458-464, vol. 32, No. 3.

Thanasis Loupas et al., "An axial velocity estimator for ultrasound flood flow imaging, based on a full evaluation of the Doppler equation by means of a two-dimensional autocorrelation approach," in IEEE Transactions on Ultrasonics, Ferroelectrics, and Frequency Control, Jul. 1, 1995, doi: 10.1109/58.393110, pp. 672-688, vol. 42, No. 4.

Notice of Allowance dated May 11, 2022 for U.S. Appl. No. 17/080,527.

Non-Final Office Action dated Dec. 9, 2021 for U.S. Appl. No. 17/080,527.

* cited by examiner

ADAPTIVE SELECTION OF ULTRASOUND FREQUENCY

CROSS REFERENCE TO RELATED APPLICATIONS

This application claims the benefit of U.S. Provisional Application Ser. No. 62/925,491, filed Oct. 24, 2019, entitled "Adaptive Ultrasound Frequency Selection", which is incorporated herein by reference. If there are any contradictions or inconsistencies in language between this application and one or more of the cases that have been incorporated by reference that might affect the interpretation of the claims in this case, the claims in this case should be interpreted to be consistent with the language in this case.

STATEMENT REGARDING FEDERALLY SPONSORED RESEARCH

This invention was made with Government support under Grant No. R01EB026574 awarded by the National Institutes of Health. The Government has certain rights in the invention.

FIELD OF THE INVENTION

The present invention relates to ultrasound systems in general, and, more particularly, selecting an optimal frequency in an ultrasound system to acquire images for clinical use during a normal scanning procedure.

BACKGROUND OF THE INVENTION

Ultrasound imaging can be performed through pulse-echo events. An acoustic wave can be emitted from an array of piezoelectric elements, propagated through tissue in a selected acoustic window, and reflected back to the array elements. Adaptive imaging in ultrasound refers to selecting parameters for imaging or processing on either a patient-to-patient or frame-to-frame basis.

Under Lag-One-Coherence (LOC), pilot pulses can be transmitted over a range of different frequencies, or a frequency sweep, and the received echo data is processed to calculate the coherence and the expected target conspicuity in different tissue environments. A chosen frequency can be used to acquire images for clinical use.

In another example, fuzzy logic can be used to adjust system parameters. The system parameters can include transmit control, receiver gain control, receive focusing, and image focusing parameters. Fuzzy logic can be applied to systems with multi-valued inputs, wherein the fuzzy logic relies on observed changes with prescribed inputs. Fuzzy logic can also be applied to neural networks to optimize parameter selection.

In another example, coherence metrics can be used to select imaging parameters. A coherence factor can be an efficient way of measuring an overall similarity of channels that are received on the transducer array within a control system. Additional measures of image quality are optimized in relation to target conspicuity.

In yet another example, frequency domain filters can be applied. The frequency domain filters can be applied in parallel to received echo data. Frequency compounding can occur to improve image quality from a predetermined set of waveforms.

In another example, harmonic imaging can reduce clutter that originates from reverberation within near-field tissue layers. However, harmonic images are still vulnerable to phase aberration. As such, the harmonic images can still retain residual clutter than can affect the image contrast and the target detail of the ultrasound image.

Although several methods exist using adaptive techniques to utilize coherence-based metrics to select an image, none of the current methods exist for real-time imaging. There is a need to use coherence-based metrics to calculate spatial coherence values, and then determine an optimal frequency to obtain clinical images without the clutter that can remain in images using the methods described above.

Further, there is need to extend beyond the LOC on real-time adaptive frequencies, in which frequencies are selected from pilot pulses, where the pilot pulses are transmitted over a wide range of frequencies via a frequency sweep and a coherence is calculated to obtain a frequency to be used to acquire images for clinical use.

SUMMARY OF THE INVENTION

The present invention enables an ultrasound system to identify and employ a frequency that enables an improved ability to acquire high-quality clinical images in real time without some of the costs and disadvantages of the prior art. Embodiments of the present invention typically employ general components of an ultrasound system such as a transducer, and a control system that includes a bandpass filter and a processor.

An aspect of the present invention is an ultrasound system for ensuring high ultrasound image quality. The ultrasound system can include the transducer, wherein the transducer is configured to transmit and receive ultrasound signals. The control system within the ultrasound system can be configured to control the transducer. Moreover, after channel ensemble or pulse-echo data is acquired in a frequency bandwidth of interest, the signal of the pulse-echo data is bandpass-filtered through a bandpass filter within the control system. The signal is bandpass-filtered over a variety of frequency ranges which either match a transmit frequency or span a bandwidth of excitation.

A processor within the control system can determine the spatial coherence of the bandpass-filtered signal by a spatial domain approach or a frequency domain approach. Further, the processor can predict a target conspicuity, and accordingly, select a preferred frequency based on the predicted target conspicuity. In some embodiments, the preferred frequency is selected so as to realize the predicted target conspicuity.

In marked contrast to the prior art, embodiments of the present invention mitigate acoustic clutter such that they do not share the typical problems of acoustic clutter that can contribute to poor quality ultrasound images. Clutter can reduce a visibility/conspicuity of imaging targets. The clutter can lead to decreased image contrast and obscure target detail with often a grainy texture. Such clutter can include reverberation, phase aberration, and also off-axis scattering from bright reflectors. As such, in accordance with the present disclosure, the removal/mitigation of clutter enables enhanced image contrast and less obscured target detail thereby enabling improved ultrasound images.

An illustrative embodiment of the present invention is an ultrasound system comprising a transducer configured to acquire pulse-echo data at each transmit frequency bandwidth of interest. A bandpass filter can be configured to receive a signal of the pulse-echo data, in which the signal is bandpass-filtered over a plurality of frequencies. A processor is configured to calculate a spatial coherence of the bandpass-filtered signal. The spatial coherence is calculated in a spatial domain or a frequency domain and used to predict a target conspicuity. The processor then selects a preferred frequency based on the predicted target conspicuity, where the goal is to realize this predicted target conspicuity.

In some embodiments, the signal of the pulse-echo data is bandpass-filtered over a plurality of frequencies that match its transmit frequency.

In some embodiments, the pulse-echo data signal is bandpass-filtered over a plurality of frequencies that span a bandwidth of excitation, wherein a plurality of frequencies spans the bandwidth of excitation by means of coded excitation, such as a chirp transmission.

In some embodiments, scanning of images occurs at the selected preferred frequency.

In some embodiments, the target conspicuity includes a balance of image contrast, image resolution, and a target size.

An embodiment of the present invention is an ultrasound system comprising: a transducer configured to transmit pulse signals and receive pulse-echo data; a band pass filter configured to receive pulse-echo data from the transducer, wherein a signal of the pulse-echo data is bandpass-filtered over frequency ranges that match a transmit frequency of the pulse-echo data; and a processor configured to calculate a spatial coherence of the bandpass-filtered signal, wherein the spatial coherence is a image quality predictor of the signal, and wherein the processor uses the calculated spatial coherence to obtain a preferred frequency.

In some embodiments, the processor obtains the preferred frequency based on a prediction of a target conspicuity.

In some embodiments, the spatial coherence includes a spatial separation of two or more points of the band-pass filtered signal.

In some embodiments, the processor utilizes a short-time Fourier transform of the band-pass filtered signal to calculate the spatial coherence.

In some embodiments, the processor calculates a normalized cross-correlation between all combinations of channel pairs over an axial kernel to calculate the spatial coherence.

Another embodiment of the present invention is a method comprising selecting a preferred frequency for scanning. The method includes receiving, by a transducer, pulse-echo data at each transmit frequency bandwidth of interest. The method also includes bandpass-filtering a signal of the pulse-echo data by a bandpass filter, wherein the signal is bandpass-filtered over a plurality of frequencies. In addition, the method includes calculating a spatial coherence of the bandpass-filtered signal by a processor, wherein the spatial coherence of the signal is calculated in a spatial domain or frequency domain. The spatial coherence is used to predict a target conspicuity, wherein the processor selects a preferred frequency based on the predicted target conspicuity. In some embodiments, the preferred frequency is selected so as to realize the predicted target conspicuity.

In some embodiments, the signal of the pulse-echo data is bandpass-filtered over the plurality of frequencies that span a bandwidth of excitation.

In some embodiments, the spatial coherence involves a spatial separation of two points in which a normalized spatial coherence function is calculated.

In some embodiments, the spatial coherence is obtained by calculating a normalized cross-correlation between all combinations of channel pairs over an axial kernel and/or by performing a short-time Fourier transform on the bandpass-filtered signal in a channel domain.

In some embodiments, the target conspicuity is calculated by using a contrast and a diameter of a target, and a number of independent images to be spatially compounded.

DETAILED DESCRIPTION

Figure 1:
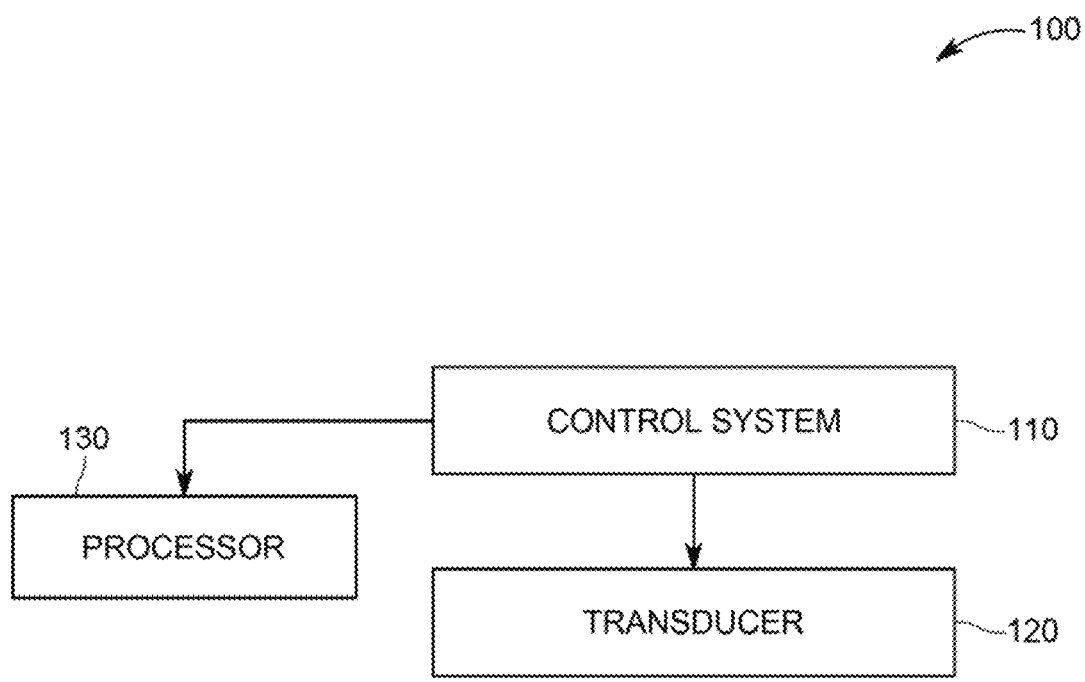
FIG. 1 depicts a block diagram of an ultrasound system in accordance with an illustrative embodiment of the present invention.

FIG. 1 depicts a block diagram of an ultrasound system 100. The ultrasound system 100 includes a control system 110, a transducer 120, and a processor 130. The control system 110 includes all of the necessary configurations of a typical ultrasound system 100. Moreover, the control system 110 includes, input/output devices, a display, memory, a bandpass filter, a power source, and other necessary configurations that are generally configured within an ultrasound system 100. Accordingly, the control system 110 can include all necessary elements that are necessary to obtain a preferred frequency to be used to acquire images for clinical use.

In an embodiment, the transducer 120 is a conventional ultrasound transducer that can acquire ensemble channel data and or pulse-echo data. A conventional ultrasound transducer is also known as a probe that produces sound waves that bounce off of body tissues and make echoes. Further, conventional transducer can send the produced echoes to enable an image known as a sonogram to be created.

Three common types of ultrasound transducers with piezoelectric crystal arrangements include a linear transducer, a convex transducer, and a phased array transducer. The linear transducer is made up of a linear piezoelectric crystal arrangement, and used for two-dimensional and three-dimensional imaging. Another common ultrasound transducer includes a convex transducer or curve transducer to due its curvilinear piezo electrical crystal arrangement. The convex transducer can also be used for two-dimensional and three-dimensional imaging. Yet another type of ultrasound transducer can include is a phased array transducer that is named after a piezo electrical arrangement also known as a phased-array. The phased array transducer can also be used for two-dimensional and three-dimensional imaging.

The transducer 120 can transmit the pulse-echo data onto the control system 110. The control system 110 can receive the echo data from the transducer 120, and transmit a signal of the pulse-echo data onto a bandpass filter. The bandpass filter within the control system 110 can filter a signal of the echo data. The bandpass filter can filter the signal over a variety of frequency ranges. The frequency of ranges can either match the transmit frequency or span the bandwidth of excitation. The processor 130 configured within the control system 110 can then calculate the spatial coherence of the bandpass-filtered signal. The processor can calculate the spatial coherence of the bandpass-filtered signal using a spatial domain approach or a frequency domain approach. The processor can use the calculated spatial coherence to predict a target conspicuity. The processor can then select the preferred frequency based on the predicted target conspicuity—preferably, the preferred frequency is selected so as to substantially realize the predicted target conspicuity. The preferred frequency refers to a target, optimum, or extremum (e.g., highest or lowest) frequency that is available.

In addition to a preferred frequency, a frequency bandwidth can be selected with selectable upper-cutoff frequencies, lower-cutoff frequencies and an arbitrary spectrum shape. A kernel or region-of-interest over which the echo data for frequency bandwidth selection is selected can have variable axial and lateral size and can also be adaptively selected from a larger region. Adaptive frequency bandwidth selection can be used to obtain improved image quality. Moreover, adaptive frequency bandwidth selection can be used to define the frequency bandwidth for tasks such as elastography measurements, Doppler imaging measurements, and quantitative ultrasound measurements.

The adaptive frequency selection technique could be used to select the frequency bandwidth for fundamental or harmonic imaging to determine which of the two methods yields a better target conspicuity. In addition, the adaptive frequency selection technique can also be used to determine if a combination of fundamental and harmonic echoes yields better image quality than either technique used on its own.

Figure 2:
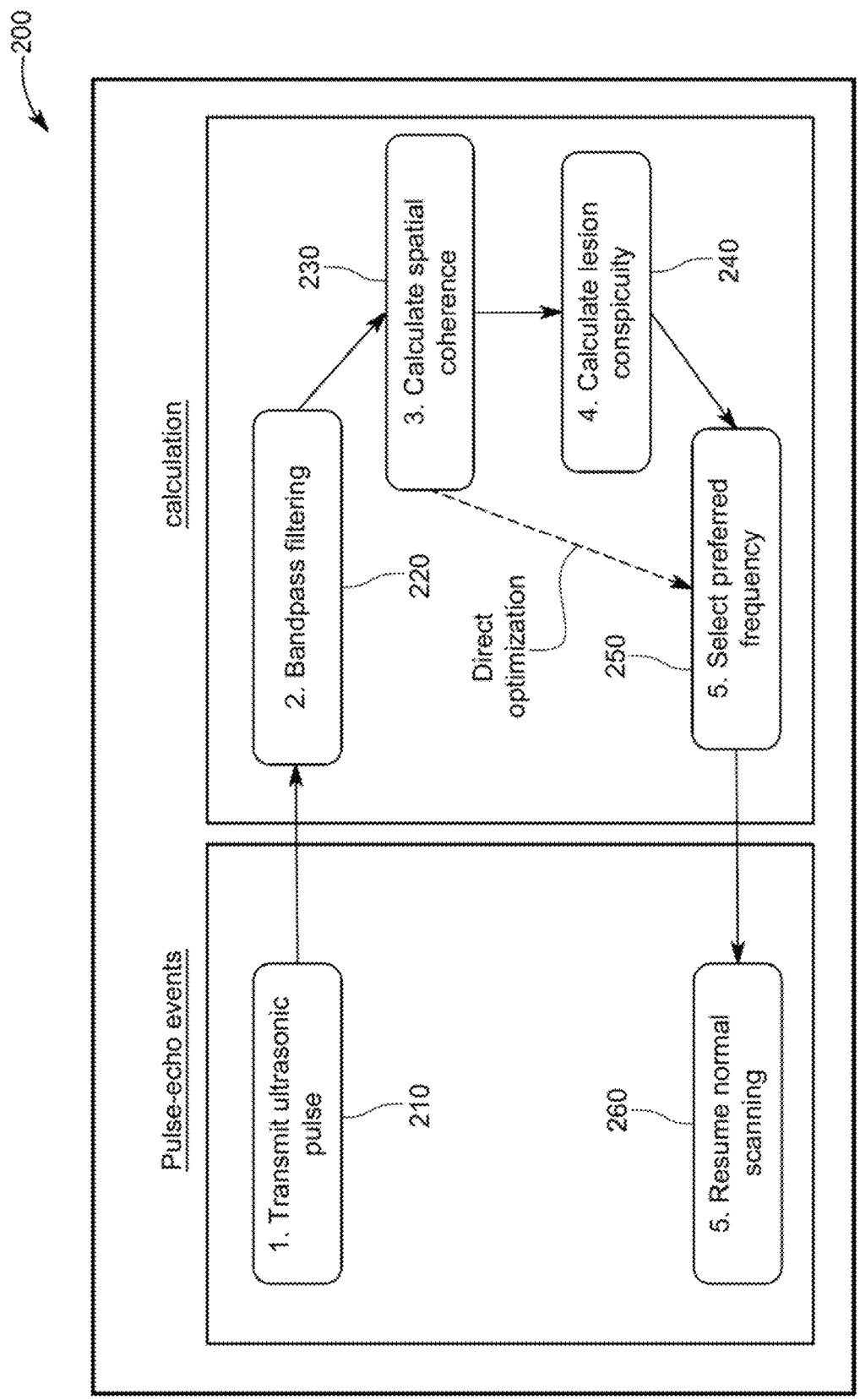
FIG. 2 shows a block diagram of an example workflow in accordance with an illustrative embodiment of the present invention.

An example workflow for the ultrasound system 100 is illustrated and described in detail in FIG. 2.

FIG. 2 depicts block diagram of an example workflow of an ultrasound system 200. The example workflow illustrates the process that the transducer 120, control system 110, and processor 130 within the ultrasound system 200 can perform to acquire pulse-echo data, bandpass filter a signal of the pulse-echo data, calculate a spatial coherence of the bandpass filtered signal, predict a target conspicuity, and identify a preferred frequency based on the predicted target conspicuity.

The transducer 120 within the ultrasound system 200 can acquire pulse-echo data. The transducer 120 can acquire the pulse-echo data at each transmit frequency bandwidth of interest in a single transmit. Moreover, in the single transmit, the pulse-echo data can be generated from either a broadband excitation or from an encoded excitation that contain the frequencies of interest. Upon acquiring the pulse-echo data, the transducer 120 can transmit a signal/ultrasonic pulse 210 of the pulse-echo data to a bandpass filter. The bandpass filter can filter 220 the pulse-echo data signal. The bandpass filter can bandpass-filter the signal over a variety of frequency ranges. In an embodiment, the bandpass filter can filter the signal of over frequency ranges that match the transmit frequency of the pulse-echo data. In another embodiment, the bandpass filter can filter the pulse-echo data signal over a frequency of ranges that span the bandwidth of excitation.

After the pulse-echo data signal is filtered through the bandpass filter, the processor 130 calculates the spatial coherence 230. Moreover, the processor 130 calculates the spatial coherence of the bandpass-filtered pulse-echo data signal. The spatial coherence can be expressed in terms of a spatial separation of two points. With an array of M elements, a normalized spatial coherence function R[m] can be calculated. Before the processor calculates the spatial coherence, the echo signals that are received at array elements have to be filtered in the frequency range of interest and also focused via applied time delays. Further, the processor can calculate the spatial coherence after echo signals that are filtered in the frequency range of interest as described above, and also focused via applied time delays. In addition, the processor 130 can calculate the spatial coherence using a spatial domain approach or a frequency domain approach.

In the spatial domain approach, a normalized cross-correlation between all combinations of channel pairs is calculated over an axial kernel. A full coherence curve is constructed based on the calculation of the normalized cross-correlation between all the combinations of channel pairs over the axial kernel.

In the frequency domain approach, a short-time Fourier transform is performed on signals in the channel domain. A sliding window is used in the time dimension to calculate a complex frequency-domain representation of the signal. Further, the complex normalized dot product is taken between channel pairs and averaged to provide a calculation or measure of similarity. It may be necessary for the processor 130 to use either the spatial domain or frequency domain approach to arrive at a coherence value that is intrinsic to target.

In addition, to the spatial domain and frequency domain approaches, the processor 130 can also calculate the spatial coherence utilizing a Sum-Absolute Difference (SAD) approaches, a Normalized SAD approach, and a Phase Difference approach using Loupas[1], Kasai[2] or other algorithms and non-normalized correlations.

1T. Loupas, J. T. Powers and R. W. Gill, "An axial velocity estimator for ultrasound flood flow imaging, based on a full evaluation of the Doppler equation by means of a two-dimensional autocorrelation approach." in IEEE Transactions on Ultrasonics, Ferroelectrics, and Frequency Control, vol 42, no. 4, pp. 672-688, July 1995, doi: 10.1109/S8.393110.

2C. Kasai, K. Namekawa, A. Koyano and R. Omoto, "Real-Time Two-Dimensional Blood Flow Imaging Using an Autocorrelation Technique." in IEEE Transactions on Sonics and Ultrasonics, vol. 32, no. 3, pp. 458-464, May 1985, doi: 10.1109/T-SU.1985.31615.

The calculated spatial coherence 230 can be used to predict/calculate a target/lesion conspicuity 240. The target conspicuity 240 can be a balance between contrast, imaging resolution, and target size for an ultrasound image. A mathematical representation of a target conspicuity metric (TCM) can be calculated with the following pair of equations: (1) $TCM = Cd\sqrt{N}/s_{cx}s_{cz}$; (2) $C = (C_0 G + C_0/SNR)/(G + C0/SNR)$. The variables for the pair of the equations can be further defined.

The target conspicuity metric includes the variables C and D that are the contrast and diameter of the target respectively. Further, N is the number of independent images that are to be either spatially or frequency compounded by either the spatial domain or frequency domain approach. In addition, $s_{cx}$ and $s_{cz}$ are the lateral and axial resolution. The $C_0$ is an assumed native contrast, while G is a beamforming gain. Lag-one coherence (LOC) can be used to estimate the received channel signal-to-noise ratio (SNR), which can estimate the imaging contrast of a target. Such targets within a patient can include, for example, a lesion of hepatocellular carcinoma. Using the target conspicuity 240 shown above, the frequencies that produce the least clutter at the start of an imaging session can be quickly and automatically identified. The frequencies that produce the least clutter are identified to ensure that frequency that is applied to ultrasound images enables each ultrasound image to have a greater image contrast and target detail.

A preferred frequency 250 can be chosen based on the predicted target conspicuity 240. The preferred frequency 250 can also be chosen to substantially realize the predicted target conspicuity 240. Further, once the preferred frequency 250 is chosen, normal scanning 260 can resume using the selected preferred frequency 250. The normal scanning 260 can use the preferred frequency 250 for acquiring clinical images for clinical use on one or more patients. Other modes can include any mode operating on pulse-echo data such as brightness (B) mode or Doppler modes that use a low-fixed filter or a high-fixed filter. The preferred frequency 250 gives rise to acquired clinical images that typically have greater target conspicuity than images acquired in a default frequency. In addition, the process of identifying and selecting the preferred frequency 250 can be performed for every n frames or continuously in real-time. Moreover, the frequency adjustment could also be initiated by the operator or by some operator action such as the image storage or the adjustment of some other parameter.

Further, as mentioned for FIG. 1, a frequency bandwidth can be selected with selectable upper-cutoff frequencies, lower-cutoff frequencies and an arbitrary spectrum shape. The kernel or region-of-interest over which the echo data for frequency bandwidth selection is selected can have variable axial and lateral size and be adaptively selected from a larger region. Adaptive frequency bandwidth selection can be used to obtain improved image quality. Moreover, the adaptive frequency bandwidth selection can be used to define the frequency bandwidth for elastography measurements, Doppler imaging measurements, and quantitative ultrasound measurements.

Figure 3A:
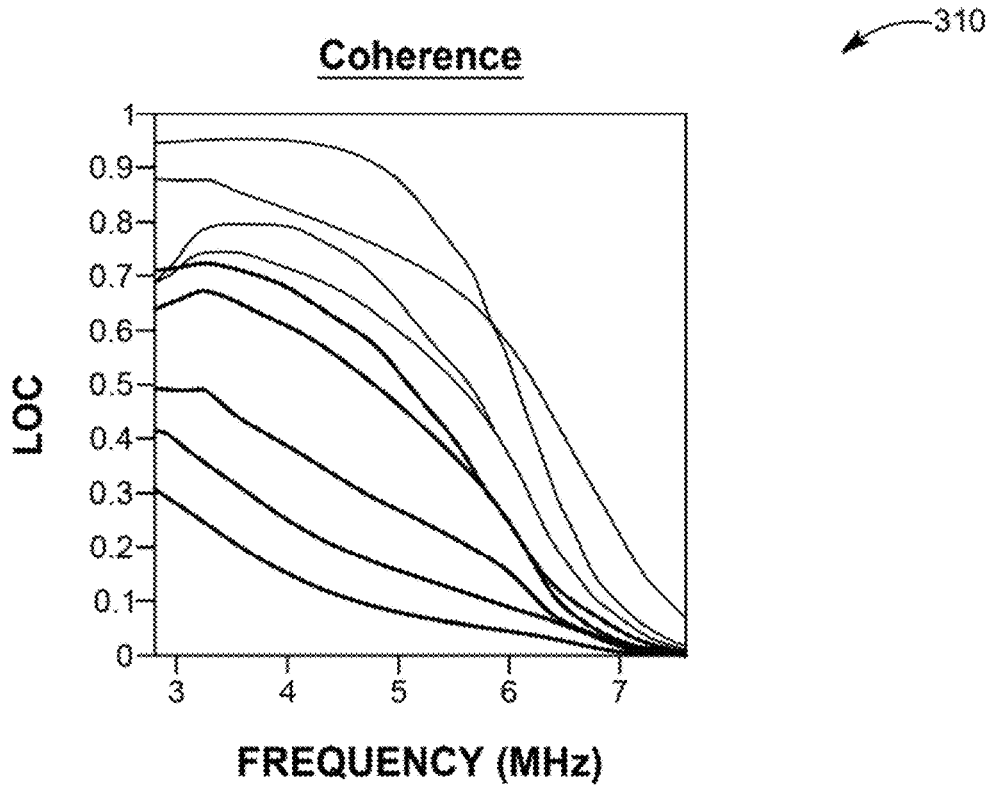
FIG. 3(A) shows graphs illustrations of spatial coherence curves and lesion conspicuity curves in accordance with an illustrative embodiment of the present invention.
Figure 3B:
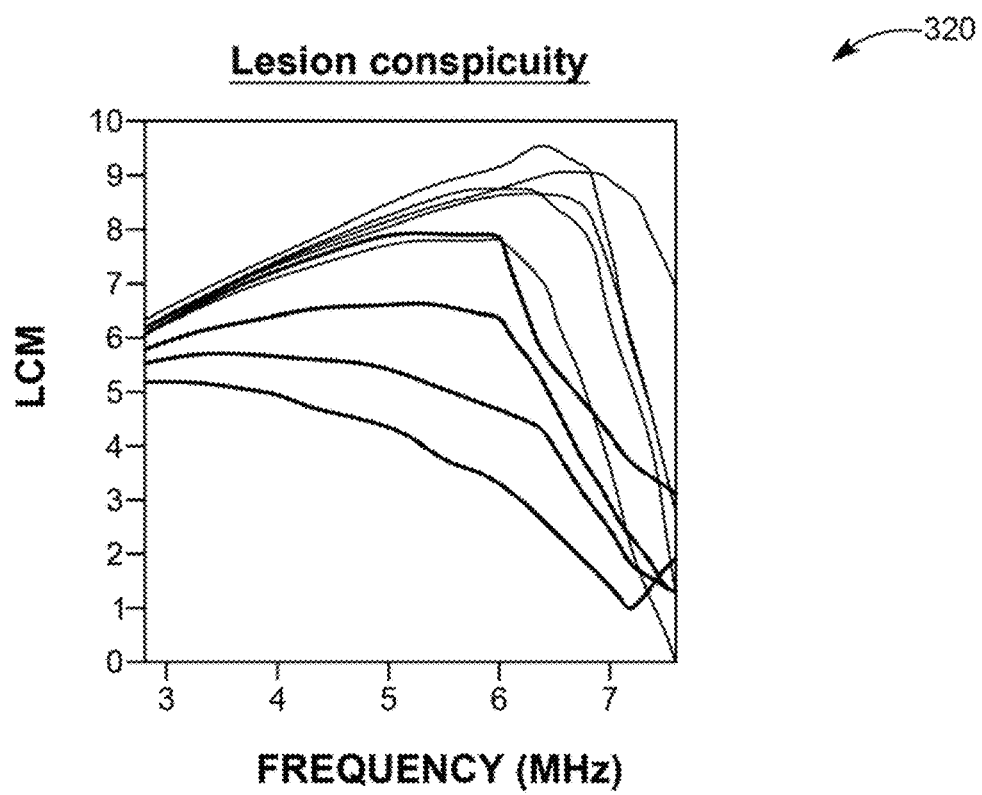
FIG. 3(B) shows illustrations of lesion/target conspicuity curves in accordance with an illustrative embodiment of the present invention.

FIGS. 3(A) and 3(B) show illustrations of LOC curves 310 and lesion conspicuity metric (LCM) curves 320 respectively. As described above, scanner parameters based on image quality can be selected. The processor within a control system of an ultrasound system can assess image quality in real-time. Contrast and contrast-to-noise ratio (CNR) require at least two regions-of-interest (ROI). A spatial coherence derived metric and a single ROI can be used to calculate the lesion/target conspicuity metric (LCM/TCM). Moreover, a frequency sweep can occur to calculate spatial coherence and target/lesion conspicuity curves. As described above, the target/lesion conspicuity curve can be used to determine a preferred frequency $f_{preferred}$. Accordingly, the LOC curves 310 that are determined from the frequency sweep can predict the LCM curves 320 that are illustrated in FIG. 3(B), and which can be also be calculated by the equations described above in FIG. 2. The LCM curves 320 can thereby be used to select a preferred frequency. The preferred frequency can be selected based on the predicted target conspicuity (preferably, to realize the predicted target conspicuity), and also be used to acquire images for clinical use during normal scanning procedures.

In summary, the process described above in FIGS. 1-3(B) leads to calculating spatial coherence values of an echo data signal filtered through a bandpass filter. The spatial coherence of the filtered echo data signal is calculated in the spatial domain approach, in which the normalized cross-correlation between all combinations of channel pairs is calculated over a chosen axial kernel to construct the full coherence curve. In the alternative, the spatial coherence of the filtered echo data signal is calculated in the frequency domain, wherein a short-time Fourier transform is performed on signals in the channel domain to calculate the complex frequency-domain representation of the signal. The complex normalized dot product is taken between channel pairs and averaged to provide a measure of similarity. Using either the spatial domain or frequency domain approach can provide the spatial coherence value needed to predict a target/lesion conspicuity. Further, the target/lesion conspicuity can be used to select a preferred frequency. The preferred frequency can be selected based on the predicted target conspicuity, and be used to acquire images for clinical use during a normal scanning procedure.

Figure 4A:
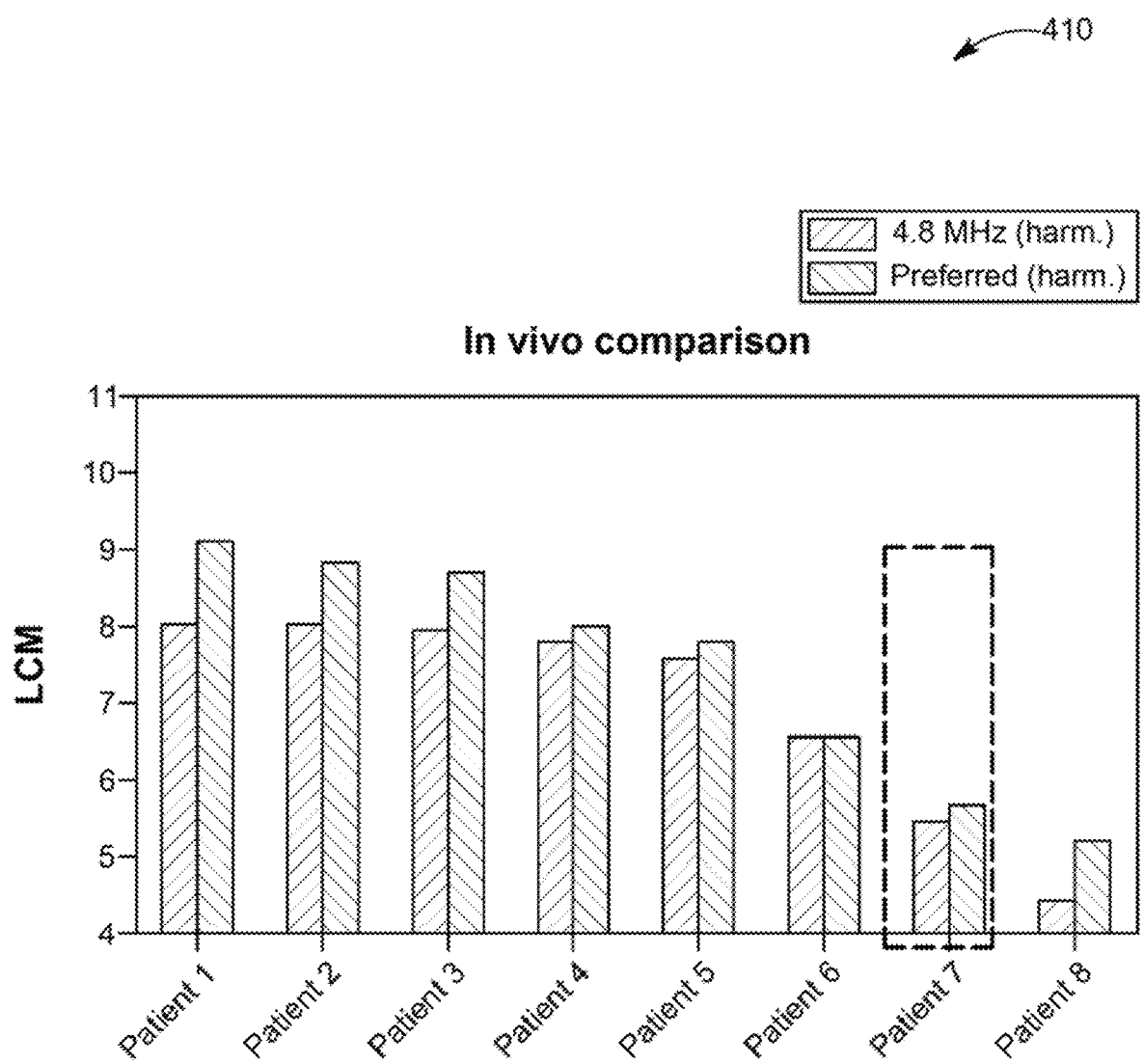
FIG. 4(A) illustrates a comparison of LCM values for patients at both a recommended frequency and a preferred frequency in accordance with an illustrative embodiment of the present invention.
Figure 4B:
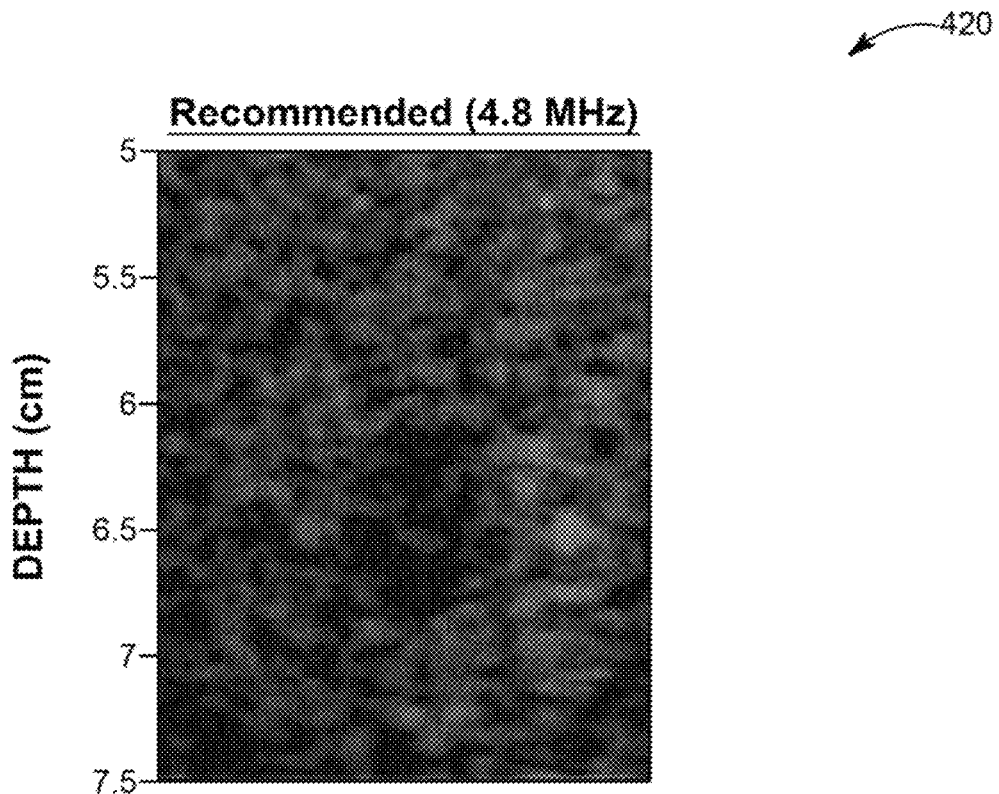
FIG. 4(B) illustrates an image contrast and target detail of an ultrasound image at a recommended frequency.
Figure 4C:
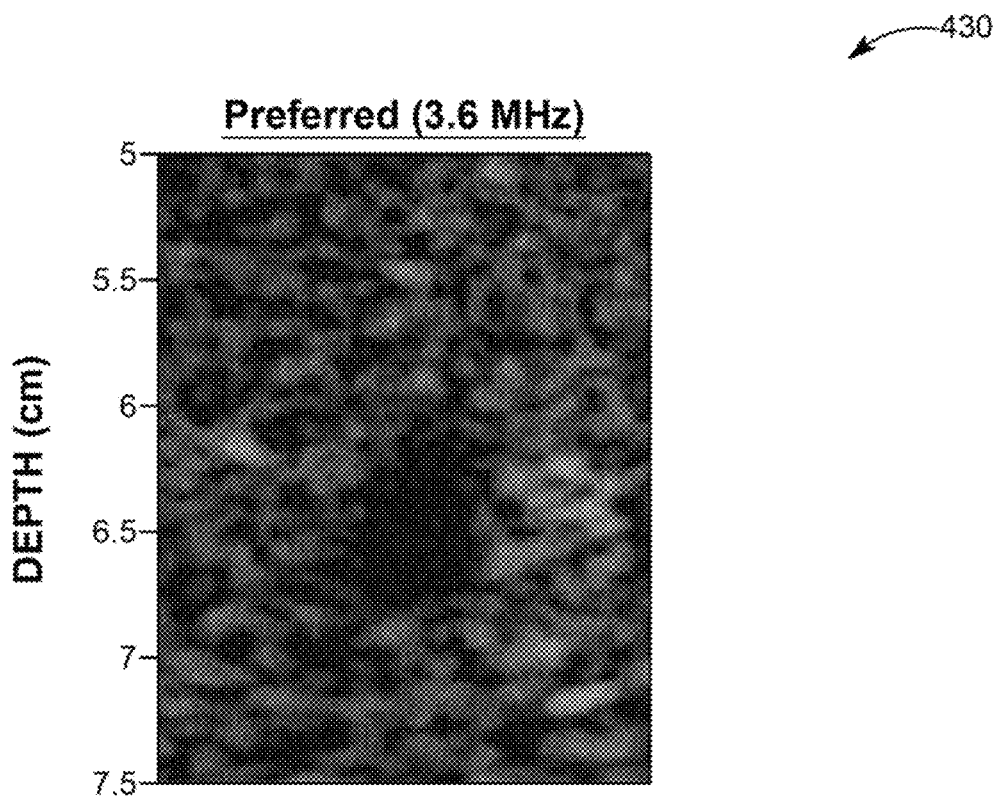
FIG. 4(C) illustrates an image contrast and target detail of an ultrasound image at a preferred frequency in accordance with an illustrative embodiment of the present invention.

FIG. 4(A)-(C) shows images that illustrate a result of applying a preferred frequency to figures for clinical use. More specifically, FIG. 4(A) illustrates an in vivo comparison 410 between of LCM values for patients at both a recommended frequency and preferred frequency. For each of the eight patients, the recommended frequency is 4.8 MHz, while the preferred frequency for each patient will be different from the recommended frequency. In the depicted example, patient no. 7 has a preferred frequency of 3.6 MHz. For each patient, the LCM value is greater at the preferred frequency as opposed to the recommended frequency (4.8 MHz). As mentioned above, the preferred frequency is selected based on the predicted/target LCM—typically, to try to ensure that the predicted/target LCM is realized. As such the preferred frequency can lead to a greater LCM than a recommended frequency that may not have been selected based on the predicted/target LCM. Further, the imaging contrast and target detail is likely to be greater for images selected using the preferred frequency as opposed to a recommended frequency.

In FIG. 4(B), an image 420 at the recommended frequency (4.8 MHz) is illustrated. Unlike an image that is selected at a preferred frequency, the image at a recommended frequency is likely to have less target conspicuity within its image. As a result, the clutter can affect the image contrast and the target detail of the image 420, wherein the image 420 is likely to have less image contrast and target detail. It is likely that the recommended frequency is not adaptively selected based on the predicted LCM or target conspicuity. As a result, the image contrast and target detail of the image 420 is more likely to be affected by clutter.

In FIG. 4(C), an image 430 at the preferred frequency (3.6 MHz) is also shown. Unlike the image 420 illustrated in FIG. 4(B), the image 430 is at a preferred frequency. The preferred frequency is selected based on the predicted LCM or target conspicuity. The image 430 also has an effective suppression of clutter that can affect the image contrast and target detail of the image 430. As a result, the image 430 has much greater image contrast and target detail than the image 420 at the recommended frequency, as well as other images that are not acquired with a preferred frequency.

A comparison of the images 420, 430 also illustrates what is also shown with the comparison of the LCM values of the eight patients in the in vivo optimization comparison 410. The LCM value for each of the eight patients at the preferred frequency was greater than the LCM value for each of the eight patients at the recommended frequency. Accordingly, as with the in vivo comparison 410, the LCM value for the image 430 at the preferred frequency (3.6 MHz) is greater than LCM value for the image 420 at the recommended frequency (4.8 MHz). Since the image 430 at the preferred frequency has a greater LCM value, the image 430 provides an image contrast and target detail that is much more visible and apparent. Moreover, as illustrated, the image contrast and target detail within the image 430 in FIG. 4(C) with the preferred frequency appears to be much less affected by clutter than the image contrast and target detail within the image 420 in FIG. 4(B) at the recommended frequency.

Figure 5:
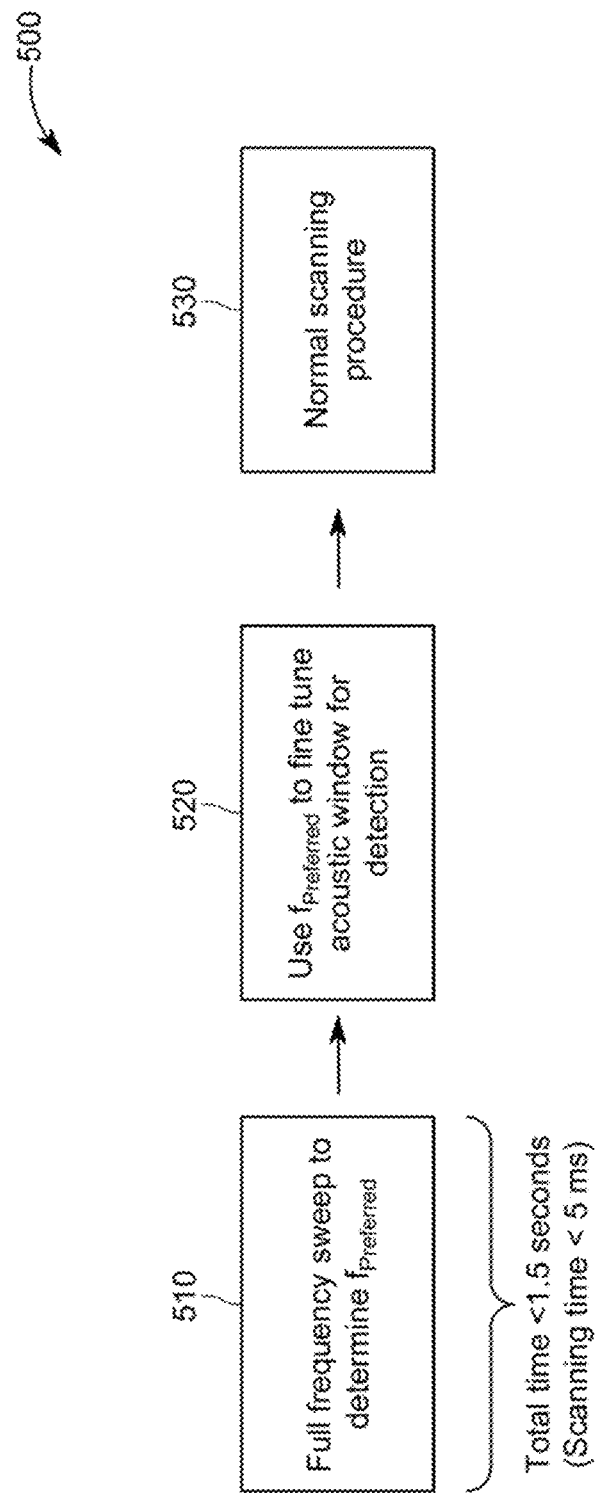
FIG. 5 depicts a flow diagram for selecting a preferred frequency and applying the preferred frequency to normal scanning procedures in accordance with an illustrative embodiment of the present invention.

In summary, the greater target LCM value can lead to a best frequency that can be used to help provide more optimal clinical images as shown with the image 430 at the preferred frequency (3.6 MHz). The higher LCM values lead to an image quality of a target area that is noticeably better with better border delineation and improved contrast at the best frequency as opposed to the recommended frequency FIG. 5 illustrates a proposed clinical implementation 500. The proposed clinical implementation 500 can include the process that leads to filtering an echo data signal through a bandpass filter over a variety of frequency ranges within an ultrasound system. As such, a full frequency sweep 510 to determine a preferred frequency is illustrated. The full frequency sweep 510 can illustrate the methods and processes described above in FIGS. 1-3.

A frequency sweep occurs when pilot pulses are transmitted over a range of different frequencies. The received echo data is processed offline to calculate the coherence and expected target conspicuity in different tissue environments. Accordingly, the frequency that is selected for acquiring the images for clinical use is based on a predicted target conspicuity with more efficient variations of calibration data acquisition and coherence calculation being applied. The transmit frequency of the pulse and related signal processing of the received echoes are chosen to get a preferred quality of signals received in the echo to enable for a real-time selection of a preferred imaging frequency.

After echo data is acquired and passed into a control system of the ultrasound system, the echo data signal is filtered through a bandpass filter over a variety of frequency ranges. The frequency ranges can either match the transmit frequency of the echo data signal or span the bandwidth excitation. The filtered echo data signal can be used to calculate the spatial coherence value using the frequency or spatial domain approach described above. The calculated spatial coherence value can in turn be used to predict a target/lesion conspicuity metric (TCM/LCM) as described above. The TCM can be used to choose a preferred frequency. The preferred frequency can be selected based on the predicted target conspicuity. As mentioned above in FIG. 1, the preferred frequency can be the target, maximum, optimum, or extremum (e.g., the highest, or lowest) frequency that is available. The total time for the full frequency sweep 510 can be 1.5 seconds (s) or less, wherein the scanning time can 5 milliseconds (ms) or less. The frequency sweep 510 is performed in real-time. In addition, the total time of echo data events that are required for the preferred frequency selection do not exceed mere fractions of a second. As such, the necessary calculations can be computed within an appropriate time frame.

A process 520 for fine-tuning an acoustic window for detection using the selected preferred frequency is also illustrated. The preferred frequency can be used to identify a target area/window for a clinical image in which image resolution and contrast of the target area can be improved as a result of the preferred frequency. The clutter within the image will be effectively suppressed to allow for an image with greater image contrast and target detail.

A normal scanning procedure 530 is also shown. In the normal scanning procedure 530, the selected preferred frequency is used to select images for clinical use. The preferred frequency will provide the images with better image resolution, contrast and target detail because the preferred frequency is used to acquire the images during the normal scanning procedure 530. As such, the preferred frequency can enable clinical images to be acquired in which the target areas of the clinical images can be seen with better image resolution and contrast than images selected acquired without the preferred frequency.

Figure 6:
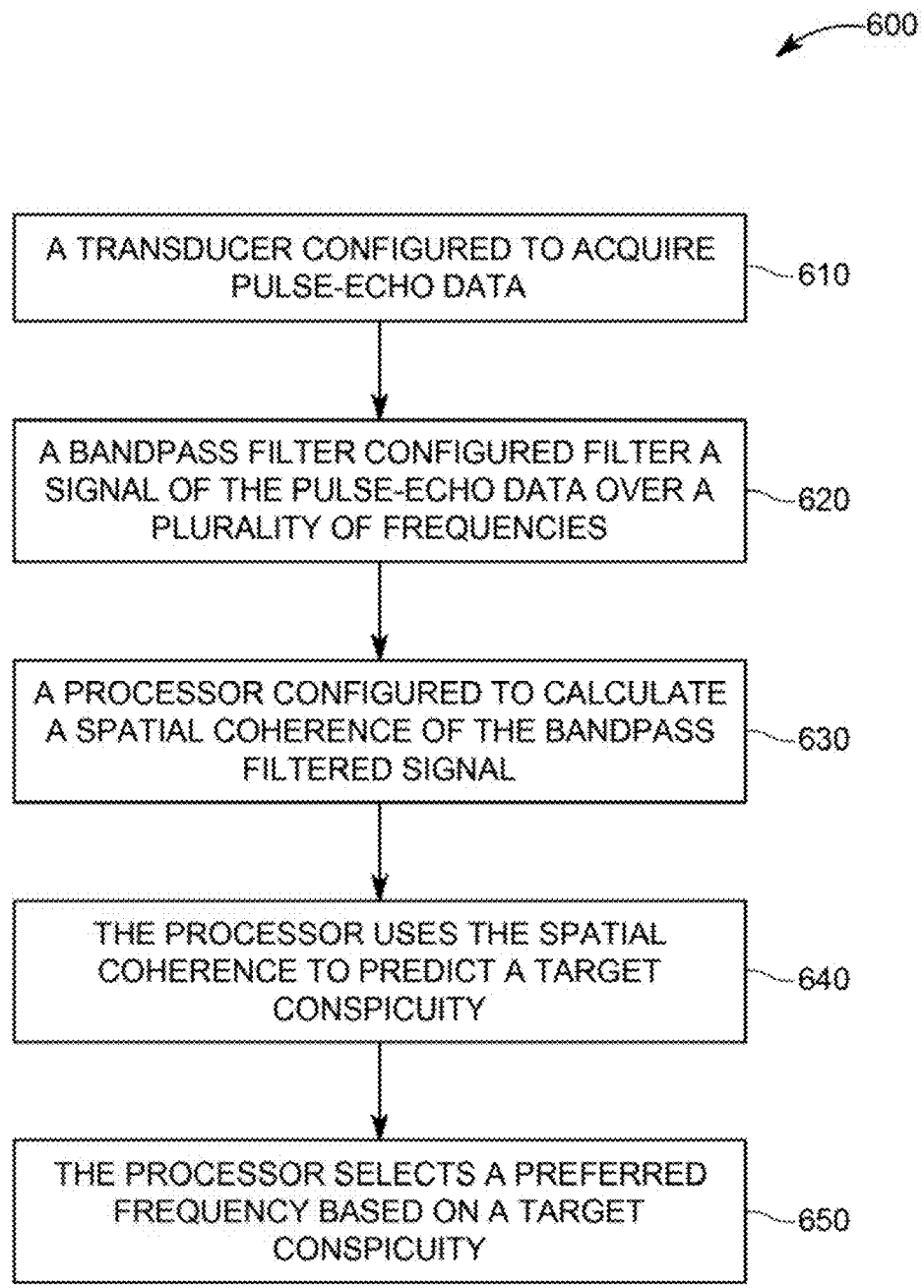
FIG. 6 illustrates a flowchart that illustrates the process in which a best frequency is selected within the ultrasound system in accordance with an illustrative embodiment of the present invention.

FIG. 6 illustrates a procedure/process 600 of selecting a preferred frequency and using that preferred frequency to acquire images for clinical use within an ultrasound system. The process can occur in an ultrasound system 100, 200 that is depicted in FIGS. 1 and 2.

Operation 610 illustrates that the transducer 120 within in an ultrasound system 100 is configured to acquire pulse-echo data. Calibration data can be acquired at a variety of frequencies. The transducer 120 can acquire the pulse-echo data at each transmit frequency bandwidth of interest. The transducer 120 can acquire the pulse-echo data in a single transmit. Moreover, in a single transmit case, the emitted waveform can be generated from a broadband excitation. In addition, the single transmit case can be encoded from an encoded excitation that contain the frequencies of interest. The transducer 120 acquires the pulse-echo data to begin the process of finding a preferred frequency to use to acquire images for clinical use in normal scanning procedures. The transducer 120 transmits the pulse-echo data to the control system.

Operation 620 depicts a bandpass filter configured to receive the pulse-echo data and filter the pulse-echo data over a variety of frequency ranges. The control system 110 within the ultrasound system 100 receives the pulse-echo data from the transducer 120. The signal of the pulse-echo data is passed thru a bandpass filter that can be configured within the control system 110 of the ultrasound system. The bandpass filter can filter the pulse-echo data signal. The pulse-echo data signal can be bandpass-filtered over a variety of frequency ranges. The frequency ranges can match the transmit frequency. In addition, or in other embodiments, the frequency ranges can also span the bandwidth of excitation. Moreover, a plurality of frequencies span the bandwidth of excitation by means of coded excitation methods such as a chirp transmission. The pulse-echo data signal is passed through the bandpass filter so that the spatial coherence of the signal can be calculated. Accordingly, the filtering process can thereby produce a bandpass-filtered signal of the pulse-echo data to allow the spatial coherence of the bandpass-filtered signal to be calculated.

Operation 630 illustrates the processor 130 configured to calculate the spatial coherence of the bandpass-filtered signal. The processor 130 configured within the control system 110 within the ultrasound system 100 can calculate the spatial coherence value of the bandpass filtered signal. The spatial coherence is predictive of the image quality for potential clinical images. Moreover, the spatial coherence can be interpreted as a spatial separation of two points. The processor 130 can calculate the spatial coherence using the spatial domain approach or the frequency domain approach.

In the spatial domain approach, a full coherence curve is constructed. The full coherence curve is constructed by calculating a normalized cross-correlation between all combinations of channel pairs over a chosen axial kernel.

With the frequency domain approach, the processor 130 can use a short-time Fourier transform to be performed on signals in the channel domain. A sliding window can be used in the time dimension. A sliding window is used in the time dimension to calculate a complex frequency-domain representation of the signal. In addition, the complex normalized dot product is taken between channel pairs and averaged to provide a calculation or measure of similarity. As mentioned above, it may be necessary for the processor 130 to use either the spatial domain or frequency domain approach to arrive at a coherence value that is intrinsic to target.

In addition, processor 130 can also calculate the spatial coherence utilizing a Sum-Absolute Difference (SAD) approach, a Normalized SAD approach, and a Phase Difference approach using Loupas, Kasai or other algorithms and non-normalized correlations.

Operation 640 illustrates the processor 130 using the spatial coherence value to predict a target conspicuity. As mentioned above, the target conspicuity metric (TCM) can be mathematically illustrated by the following equations: (1) $TCM = Cd \sqrt{N}/s_{cx}s_{cz}$; (2) $C = (C_0 G + C_0/SNR)/(G + C_0/SNR)$. The processor 130 can calculate the TCM using the two equations. Identifying the TCM can enable the processor 130 to be able to identify the desired preferred frequency. The processor can identify and select the preferred frequency based on the predicted TCM or target conspicuity—preferably so that the predicted TCM or target conspicuity is realized.

Operation 650 illustrates the processor 130 is configured to select the best frequency based on the predicted target conspicuity. In some embodiments, the preferred frequency is selected so as to realize the predicted target conspicuity. Moreover, selecting the preferred frequency based on, and preferably to realize, the predicted target conspicuity can enable images to be acquired that have much greater clutter suppression, and enhanced image contrast and target detail.

In addition, as previously described above, a frequency bandwidth can be selected with selectable upper-cutoff frequencies, lower-cutoff frequencies, and an arbitrary spectrum shape. Further, as also mentioned above, a kernel or region-of-interest over which the echo data for frequency bandwidth selection is selected can have variable axial and lateral size and can also be adaptively selected from a larger region. Adaptive frequency bandwidth selection can be used for improved image quality. Moreover, adaptive frequency bandwidth selection can be used for defining the frequency bandwidth for elastography measurements, Doppler imaging measurements, and quantitative ultrasound measurements.

In summary, the described process 600 provides a method for acquiring pulse-echo data for an ultrasound system, and filtering a signal of the pulse-echo data to calculate a spatial coherence value by using a spatial domain or frequency domain approach. The calculated spatial coherence value can be used to predict a target conspicuity. A preferred frequency can then be selected based on the predicted target conspicuity, and also be used to acquire images for clinical use during a normal scanning procedure. As such, the clinical images obtained using the selected preferred frequency provide images with less clutter and greater image contrast and target detail than clinical images that use a recommended frequency or other conventional methods where more clutter would be present.

It is to be understood that the disclosure teaches just some examples of embodiments in accordance with the present invention and that many variations of the invention can easily be devised by those skilled in the art after reading this disclosure and that the scope of the present invention is to be determined by the following claims.

What is claimed is:

1. A system comprising:
   a transducer to:
   output a first ultrasonic signal that bounces off a target and produces an ultrasonic echo signal,
   receive the ultrasonic echo signal,
   convert the ultrasonic echo signal to an electrical signal that spans a frequency range and represents a first image of the target; and
   a processor to:
   obtain a set of two or more sub-signals from the electrical signal, wherein each of the sub-signals spans a respective frequency sub-range of the frequency range,
   compute, for each of the sub-signals, a respective plurality of spatial coherence metric values,
   determine, for each of the sub-signals, a respective value of a conspicuity metric based on the respective plurality of spatial coherence metric values, and
   select a frequency sub-range of the respective frequency sub-ranges based on the conspicuity metric values, wherein the selected frequency sub-range is for a second ultrasonic signal, the second ultrasonic signal for obtaining a second image.

2. The system of claim 1 wherein the second ultrasonic signal spans the entire selected frequency sub-range.

3. The system of claim 1 wherein the second ultrasonic signal is within the selected frequency sub-range and has a bandwidth less than the bandwidth of the selected frequency sub-range.

4. The system of claim 1 wherein the processor is further configured to select a single frequency within the selected frequency sub-range for the second ultrasonic signal, and wherein the single frequency is the highest frequency of the selected frequency sub-range.

5. The system of claim 1 wherein the processor is further configured to select a single frequency within the selected frequency sub-range for the second ultrasonic signal, and wherein the single frequency is the lowest frequency of the selected frequency sub-range.

6. The system of claim 1 wherein the conspicuity metric value for the sub-signal corresponding to the selected frequency sub-range is a maximum over the conspicuity metric values of the sub-signals.

7. The system of claim 1 wherein at least one of the first ultrasonic signal or the second ultrasonic signal is a pulse.

8. The system of claim 1 wherein the second image is of the same target as the first image.

9. A method comprising:
   outputting, by a transducer, a first ultrasonic signal that bounces off a target and produces an ultrasonic echo signal;
   receiving, by the transducer, the ultrasonic echo signal;
   converting, by the transducer, the ultrasonic echo signal to an electrical signal that spans a frequency range, the electrical signal representing a first image of the target;

obtaining a set of two or more sub-signals from the electrical signal, wherein each of the sub-signals spans a respective frequency sub-range of the frequency range;

computing, for each of the sub-signals, a respective plurality of spatial coherence metric values, determining respective values of a conspicuity metric for each of the sub-signals based on the respective plurality of spatial coherence metric values;

selecting a frequency sub-range of the respective frequency sub-ranges based on the conspicuity metric values; and generating a second ultrasonic signal based on the selected frequency sub-range, the second ultrasonic signal for obtaining at least one of a second image of the target or an image of a different target.

10. The method of claim 9 wherein the second ultrasonic signal spans the entire selected frequency sub-range.

11. The method of claim 9 wherein the second ultrasonic signal is within the selected frequency sub-range and has a bandwidth less than the bandwidth of the selected frequency sub-range.

12. The method of claim 9 wherein the second ultrasonic signal is a single frequency.

13. The method of claim 12 wherein the single frequency is the highest frequency of the selected frequency sub-range.

14. The method of claim 12 wherein the single frequency is the lowest frequency of the selected frequency sub-range.

15. The method of claim 9 wherein the conspicuity metric value for the sub-signal corresponding to the selected frequency sub-range is a maximum over the conspicuity metric values of the sub-signals.

* * * * *